(12) United States Patent
Heintz et al.

(10) Patent No.: US 11,633,587 B2
(45) Date of Patent: Apr. 25, 2023

(54) MIXED IONIC ELECTRONIC CONDUCTORS: DEVICES, SYSTEMS AND METHODS OF USE

(71) Applicant: Battelle Memorial Institute, Columbus, OH (US)

(72) Inventors: Amy M. Heintz, Dublin, OH (US); Krenar Shqau, Columbus, OH (US); Ramanathan Lalgudi, Westerville, OH (US); Katherine M. Palmer, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 62 days.

(21) Appl. No.: 16/597,792

(22) Filed: Oct. 9, 2019

(65) Prior Publication Data

US 2020/0038648 A1 Feb. 6, 2020

Related U.S. Application Data

(63) Continuation-in-part of application No. 16/080,303, filed as application No. PCT/US2018/026981 on Apr. 10, 2018, now Pat. No. 11,266,827.

(Continued)

(51) Int. Cl.
*A61N 1/04* (2006.01)
*A61B 5/00* (2006.01)
*A61B 5/30* (2021.01)

(52) U.S. Cl.
CPC .......... *A61N 1/0448* (2013.01); *A61B 5/0006* (2013.01); *A61B 5/30* (2021.01);

(Continued)

(58) Field of Classification Search
CPC .... A61N 1/0448; A61N 1/044; A61N 1/0496; A61N 1/0551; A61N 1/0468;

(Continued)

(56) References Cited

U.S. PATENT DOCUMENTS 4,383,529 A * 5/1983 Webster ................. A61N 1/044 604/20
5,356,632 A * 10/1994 Gross ..................... A61N 1/044 424/448

(Continued)

FOREIGN PATENT DOCUMENTS

EP 0057877 B1 10/1985
WO 2018191317 A1 10/2018

OTHER PUBLICATIONS

Pan, Yongzheng, and Lin Li. "Percolation and gel-like behavior of multiwalled carbon nanotube/polypropylene composites influenced by nanotube aspect ratio." Polymer 54.3 (2013): 1218-1226. (Year: 2013).*

(Continued)

*Primary Examiner* — Gary Jackson
*Assistant Examiner* — Alexander M Eisenberg
(74) *Attorney, Agent, or Firm* — Frank Rosenberg; Susanne A. Wilson

(57) ABSTRACT

The invention provides a variety of novel devices, systems, and methods of utilizing mixed-ionic-electronic conductor (MIEC) materials adapted to function with an applied current or potential. The materials, as part of a circuit, are placed in contact with a part of a human or nonhuman animal body. A sodium selective membrane system utilizing the MIEC is also described.

18 Claims, 9 Drawing Sheets

Related U.S. Application Data

(60) Provisional application No. 62/743,517, filed on Oct. 9, 2018.

(52) U.S. Cl.
CPC .......... *A61B 5/4041* (2013.01); *A61B 5/6824* (2013.01); *A61N 1/044* (2013.01)

(58) Field of Classification Search
CPC ...... A61N 1/0436; A61B 5/30; A61B 5/0006; A61B 5/4041; A61B 5/6824; A61B 5/259; C08J 3/215; C08J 5/02; A61F 2013/00229; B82Y 30/00; H01B 1/24
See application file for complete search history.

(56) References Cited

U.S. PATENT DOCUMENTS

| | | | |
|---|---|---|---|
| 5,376,107 A | | 12/1994 | Inagi et al. |
| 6,374,136 B1* | | 4/2002 | Murdock .............. A61N 1/0448 604/20 |
| 6,718,212 B2 | | 4/2004 | Parry et al. |
| 7,943,065 B2 | | 5/2011 | El Bounia |
| 8,862,223 B2 | | 10/2014 | Yanaki |
| 9,248,278 B2 | | 2/2016 | Crosby et al. |
| 9,253,878 B2 | | 2/2016 | Kobayashi et al. |
| 9,675,358 B2 | | 6/2017 | Wagner et al. |
| 10,010,272 B2 | | 7/2018 | Wisniewski et al. |
| 10,279,170 B2 | | 5/2019 | Syed et al. |
| 10,553,342 B2* | | 2/2020 | Lazarus ................ H01F 27/24 |
| 2005/0064209 A1* | | 3/2005 | Haines ................ C03C 17/3405 428/447 |
| 2006/0276742 A1* | | 12/2006 | Matsumura .......... A61N 1/0428 604/20 |
| 2007/0093789 A1 | | 4/2007 | Smith |
| 2010/0114273 A1 | | 5/2010 | Muccio |
| 2010/0173228 A1 | | 7/2010 | Wallace et al. |
| 2010/0190654 A1* | | 7/2010 | Rothrock .............. B01L 3/5085 506/9 |
| 2013/0244121 A1* | | 9/2013 | Gogotsi ................ H05K 9/009 429/338 |
| 2014/0090884 A1 | | 4/2014 | Kobayashi et al. |
| 2015/0182473 A1* | | 7/2015 | Bosnyak ................ A61N 5/062 514/356 |
| 2015/0357078 A1* | | 12/2015 | Lessing ................ H01R 13/52 252/511 |
| 2016/0058998 A1* | | 3/2016 | Skiba ...................... A61N 1/326 607/50 |
| 2016/0155530 A1* | | 6/2016 | Someya ................ A61B 5/686 174/257 |
| 2016/0303362 A1* | | 10/2016 | Wu ......................... A61L 15/60 |
| 2017/0273590 A1 | | 9/2017 | Maesani et al. |
| 2018/0014780 A1* | | 1/2018 | Sotzing ................ A61B 5/291 |
| 2019/0137436 A1 | | 5/2019 | Lillehoj et al. |

OTHER PUBLICATIONS

Stern R, Asari AA, Sugahara KN. Hyaluronan fragments: an information-rich system. Eur J Cell Biol. Aug. 2006;85(8):699-715. doi: 10.1016/j.ejcb.2006.05.009. Epub Jul. 5, 2006. PMID: 16822580 (Year: 2006).*

International Search Report from International Application No. PCT/US2019/055480, dated Mar. 24, 202.

Written Opinion from International Application No. PCT/US2019/055480, dated Mar. 24, 2020.

Aregueta-Robles et al., "Organic electrode coatings for next-generation neural interfaces", Frontiers in Neuroengineering, 2014, vol. 7, pp. 1-18, Graduate School of Biomedical Engineering, University of New South Wales, Sydney, NSW, Australia.

Moulton et al., "Liquid Crystal Behavior of Single-Walled Carbon Nanotubes Dispersed in Biological Hyaluronic Acid Solutions", JACS, 2007, vol. 129, No. 30, pp. 9452-9457.

Krenar et al., "Mixed Ionic Electronic Conductors for Improved Charge Transport in Electrotherapeutic Devices", 2017, Proceedings of the 2017 Design of Medical Devices Conference, ASME, Minneapolis, MN, USA.

* cited by examiner

MIEC embedded in    Adhesive
elastomer         |— 2 mm —|
Wire
Substrate   Current Collector

Fig. 7

Release of Vaccine under
applied electric field
——————————→

Fig. 8

Electrode Potential Determination

Cell Configuration:(-) CNTs el, | NaCl (0.1 mol/L) | Calomel Reference Electrode (+)

| Electrode Configuration | Solution - NaCl | Cell Potential (V) | Electrode Potential (V) |
|---|---|---|---|
| CNTs-HA | | +0.192 | +0.192 |
| CNTs-Zwitter Ionic Brushes | 0.1 mol/L | -0.167 | -0.167 |
| CNTs-NAFION Composite | | -0.020 | -0.020 |

$E = E_{ref} - E_\infty$ $$E_x = E^\alpha \frac{RT}{F} \times \ln a$$

Where: a = 0.1 mol/L

MIXED IONIC ELECTRONIC CONDUCTORS: DEVICES, SYSTEMS AND METHODS OF USE

RELATED APPLICATIONS

This application is a Continuation-In-Part of U.S. patent application Ser. No. 16/080,303 filed Aug. 27, 2018, which was a U.S. national stage filing of PCT/US18/026981 filed Apr. 10, 2018 which claimed the benefit of U.S. Provisional Patent Application Ser. No. 62/483,942 filed Apr. 10, 2017. U.S. patent application Ser. No. 16/080,303 is incorporated herein as if reproduced in full below. This application also claims the benefit of U.S. Provisional Patent Application Ser. No. 62/743,517 filed Oct. 9, 2018.

SUMMARY OF THE INVENTION

In one aspect, the invention provides a medical apparatus, comprising: an anode and a cathode; and a MIEC disposed between the anode and cathode. The MIEC comprises a drug or therapeutic agent is dispersed in an elastic MIEC comprising electrical conductor, ionic conductor, and elastomeric particles. The drug or therapeutic agents can be any one, or a combination of, the drugs or therapeutic agents described below. In some embodiments, the anode and cathode are parallel bars. Preferably, the apparatus does not contain a conductive ring. This apparatus may be used to heal wounds by passing a current through the device to resistively generate heat.

The invention also includes methods of making the MIEC wherein the drug or therapeutic agent is dispersed in an aqueous dispersion along with the high aspect ratio (at least 10× length to height and width) electrical conductor, ionic conductor, and elastomeric particles.

In another aspect, the invention provides a method of treating a human or nonhuman animal, comprising: providing an apparatus comprising a MIEC disposed between an anode and cathode; wherein the MIEC comprises an electrical conductor, ionic conductor, and elastomeric particles; applying the MIEC directly in contact with the skin of the human or nonhuman animal; and passing an electrical current through the MIEC. In some embodiments, the current heats the MIEC, preferably to a temperature in the range of 35 to 40° C. In some embodiments, the MIEC comprises a dispersed drug or therapeutic agent; and a current is passed through the MIEC increasing the permeability of the skin. In some embodiments, the MIEC is placed in direct contact with a wound in the skin. Preferably, the method does not utilize a hydrogel.

In a further aspect, the invention provides a wound healing system, comprising a dressing, wherein the dressing comprises a MIEC. The MIEC comprises a drug or therapeutic agent is dispersed in the elastic MIEC comprising CNTs, ionic conductor, and elastomeric particles. In some embodiments, the wound healing system further comprises one or any combination of the following: wherein the dressing comprises alginates; wherein the drug or therapeutic agent comprises epidermal growth factor; wherein the MIEC comprises 10-50 wt % CNT, 20-50 wt % ionic conductor, and 5-70 wt % elastomer; wherein the dressing comprises at least 20 mass % CNTs, or at least 50 mass % CNTs, or at least 70 mass % CNTs, or at least 90 mass % CNTs; or conversely, wherein the dressing comprises at most 80 mass %, 50%, 30%, or at most 20 mass % elastomer or other polymer.

In a related aspect, the invention provides a method of healing a wound, comprising: applying the dressing of in direct contact with a wound. In some embodiments, the dressing is applied to the wound by electrospinning. The invention also includes a method of healing a wound, comprising: applying the dressing over a wound and passing current through the dressing. Typically, the current resistively heats the dressing which assists the healing. The invention also includes a method of applying a dressing onto a wound, comprising applying an MIEC dispersion onto a wound and allowing the MIEC to harden. Alternatively, the MIEC can be applied onto a gauze over a wound. Preferably, the MIEC comprises CNTs, ionic conductor, and elastomeric particles.

In a further aspect, the invention provides a method of forming a deep nerve electrode, comprising: drawing a CNT fiber having a diameter of from 10 to 500 μm or, alternatively, providing a core fiber and coating the core fiber with CNTs to form a CNT fiber having a core coated with CNTs such that the core coated with CNTs has a diameter of from 10 to 500 μm; coating the fiber with a first insulating polymer, except leaving a tip exposed at the proximal end; applying a CNT/ionic conductor coating over the first polymer while leaving exposed the tip and a portion of the first polymer at the proximal end; and coating the fiber with a second insulating polymer, except leaving the tip and a portion of the first polymer and a portion of the CNT/ionic conductor coating exposed at the proximal end. In a preferred embodiment, the method further comprises: applying a second CNT/ionic conductor coating over the second insulating polymer, except leaving the tip and a portion of the first polymer and a portion of the CNT/ionic conductor coating, and a portion of the second polymer exposed at the proximal end.

In another aspect, the invention provides a deep nerve electrode, comprising: a CNT fiber core having a diameter of from 10 to 500 μm or, alternatively, a core fiber coated with CNTs such that the core coated with CNTs has a diameter of from 10 to 500 μm; a first insulating polymer coating the CNT fiber core, except leaving a tip of the CNT fiber core exposed at the proximal end; a CNT/ionic conductor coating over the first polymer that leaves exposed the tip and a portion of the first polymer at the proximal end; and a second insulating polymer coating over the CNT/ionic conductor coating, except leaving the tip and a portion of the first polymer and a portion of the CNT/ionic conductor coating exposed at the proximal end.

The invention also includes a cuff comprising a plurality of the deep nerve electrodes described herein. The invention also includes a method of recording or stimulating a nerve in a human or a nonhuman animal, comprising: inserting the deep nerve electrode of claim 3 into a nerve interfascicularly or intrafascicularly. If a core fiber is used, the core fiber is preferably an insulating polymer.

In yet another aspect, the invention provides a method of obtaining an EEG, ECG, or EMG, comprising utilizing an electrode of the type described herein, without use of a hydrogel, to obtain a measurement for an EEG, ECG, or EMG.

In another aspect, the invention provides a method of forming a dry electrode, comprising: mixing CNTs and ionic conductor and elastomer particles in an aqueous dispersion to form a CNT/ionic conductor/elastomer dispersion; providing a substrate comprising an electrical wire on the surface; depositing a conductive adhesive composition over the wire; applying the CNT/ionic conductor/elastomer dispersion over the conductive adhesive composition; and curing to harden the dispersion to make an MIEC connected to an electrical wire. The invention can include a step of curing the conductive adhesive composition prior to applying the dispersion. The electrical wire can be attached to the surface with adhesive or a mechanical fastener.

In a further aspect, the invention provides a vaccine system, comprising: an MIEC comprising a vaccine dispersed therein. The MIEC is disposed between an anode and a cathode. In some embodiments, the invention provides a microneedle skin patch comprising the vaccine system. The body of the microneedle skin patch is preferably made from MIEC. The invention also includes methods of using the vaccine system; in some preferred embodiments, the MIEC is stored in reservoirs in the body of a human or nonhuman animal.

In another aspect, the invention provides a method of delivering a vaccine using the vaccine system. In preferred embodiments, this method of storing vaccines can maintain vaccine activity with little or no refrigeration.

In another aspect, the invention provides an epicardial mesh, comprising: a mesh comprising an MIEC configured to be placed around the heart of a human or nonhuman animal; wherein the MIEC comprises an asymmetric electrical conductor, an ionic conductor, and elastomeric particles. The invention also provides a method of treating a human or nonhuman animal, comprising: placing the mesh of claim 1 around the heart of the human or nonhuman animal.

In a further aspect, the invention provides a method of sensing pressure changes within the body of a human or nonhuman animal, comprising: placing a MIEC material within the body of the human or nonhuman animal; and measuring changes of impedance through the MIEC as the body moves. In some embodiments, the method provides a MIEC precursor composition comprises a polyionic material with polymerizable side groups; injecting the MIEC precursor into a cavity, recess or channel inside the human or nonhuman animal; polymerizing the polyionic material to form an MIEC elastic solid body within, and conforming to the shape of, the cavity, recess or channel. Preferably, the MIEC comprises CNTs. The method may further comprise attaching electrical leads to the MIEC body. In some embodiments, the UV light is used to polymerize the polyionic material.

In another embodiment, the invention provides an ion sensing device, comprising: a working electrode and a reference electrode connected to opposite sides of a MIEC membrane wherein the reference electrode is shielded from the environment; and a voltage meter disposed between the working electrode and reference electrode. Preferably, the MIEC comprises CNTs. In some embodiments, the MIEC comprises HA, zwitter ionic brushes, or Nafion. The reference electrode may be shielded from the environment by encapsulation in the MIEC. In some embodiments, the MIEC membrane is bonded to a substrate. The ion sensing device can be disposed in an aqueous environment and the invention includes systems comprising the aqueous environment. The ion sensing device can be disposed in a body of a human or nonhuman animal and exposed to blood. The invention also includes a method of measuring ion concentration, comprising placing the ion sensing device of any of the above claims in an aqueous environment and detecting a voltage.

In a further embodiment, the invention provides a sensor for operation in aqueous environment, comprising: an active surface comprising a polymeric ionic conductor coated on the active surface. In some embodiments, the invention includes one or any combination of the following features: wherein the polymeric ionic conductor comprises Nafion; further comprising grafted SBMA; wherein the active surface comprises a MIEC; wherein the MIEC comprises a gradient of ionic conductors that increase in concentration with the highest concentration near the active surface; wherein the sensor is an electrochemical sensor; wherein the sensor is a sensor for surface plasmon resonance (SPR). The gradient can be prepared by layer-by-layer fabrication of the electrode.

In a further aspect, the invention provides a method of monitoring a chemical or biological process in an aqueous environment, comprising: disposing a sensor in an aqueous environment, wherein the sensor has an active surface comprising a polymeric ionic conductor coated on the active surface; and obtaining a plurality of measurements over time via the active surface in the aqueous environment. In some embodiments, the measurements comprise measurements of surface plasmon resonance.

In another aspect, the invention provides a sodium-selective membrane system, comprising: a composite comprising CNTs, HA, and a polymer; wherein the composite has a thickness of 100 μm or less, preferably 10 μm or less, and in some embodiments in the range of 1 to 20 μm; wherein the composite is disposed in a saline solution that is at least 0.01 M in Na, more preferably at least 0.1 M Na, or in the range of 0.2 to 0.9 M Na on at least one side of the membrane. In some embodiments, the membrane system has a length and width that are both at least 10× or at least 100× greater than thickness. The composite may be a MIEC as described herein. The invention also provides a method of removing sodium from a saline solution, comprising: providing the membrane of any of claims 1-3 disposed in an apparatus wherein the membrane has a feed side and a permeate side; wherein the saline solution on the feed side is compressed; and wherein sodium selectively passes through the membrane; e.g., the proportion of Na passing through the membrane is at least 2×, 5×, or 10× greater than Ca passing through the membrane.

Any of the above aspects may include, in various embodiments, any of the features or any combination of the features provided in the descriptions herein. The invention includes devices, methods of using devices to treat humans or nonhuman animals. The invention also includes systems that comprise devices in combination with the materials and conditions in which the devices are used.

BRIEF DESCRIPTION OF THE DRAWINGS

FIG. 7 illustrates an assembly in which a wire is attached to the substrate with adhesive, leaving enough to form a connection exposed. On top of this is then added silver adhesive, labeled "current collector" in the figure. The silver is allowed to cure. Next a MIEC/elastomer dispersion is applied to that Ag adhesive surface and cured. After curing, this surface becomes the contact with the skin.

FIG. 8 is a schematic illustration of MIEC containing vaccine and on demand delivery under an applied electric field.

DESCRIPTION OF MIECS

Mixed-ionic-electronic conductors (MIECs) are an interconnected network of electrical and ionic conductors in an elastomeric matrix that provide: (1) high surface area for efficient capacitive charge-discharge; (2) high ionic conductivity for low interfacial charge transfer—where the interfacial charge transfer can be viewed as made up of resistive and capacitive response; (3) low ohmic resistance; and (4) excellent flexibility and toughness.

Electrical and ionic conductors are embedded in a matrix in such a way that the electrical and ionic elements achieve percolation, i.e., a continuous interconnected network, at lower loading than would be achieved by simple random mixing. This allows superior electrical performance to be achieved while retaining good mechanical properties.

Figure 1:
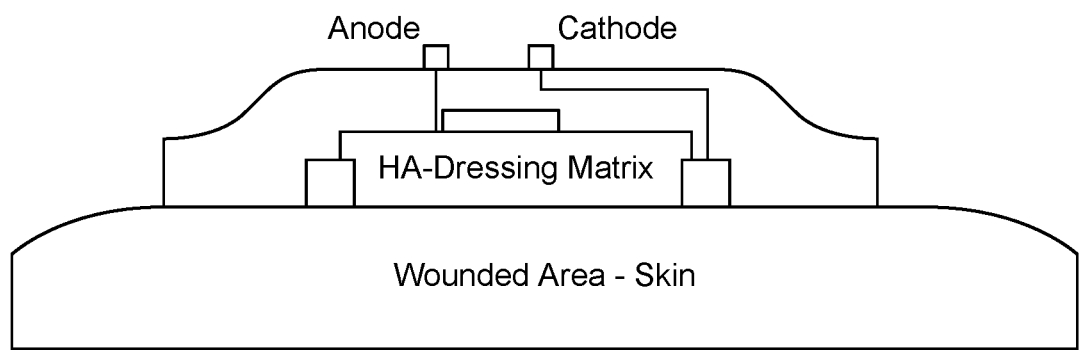
FIG. 1 schematically illustrates an apparatus for iontophoresis.
Figure 2:
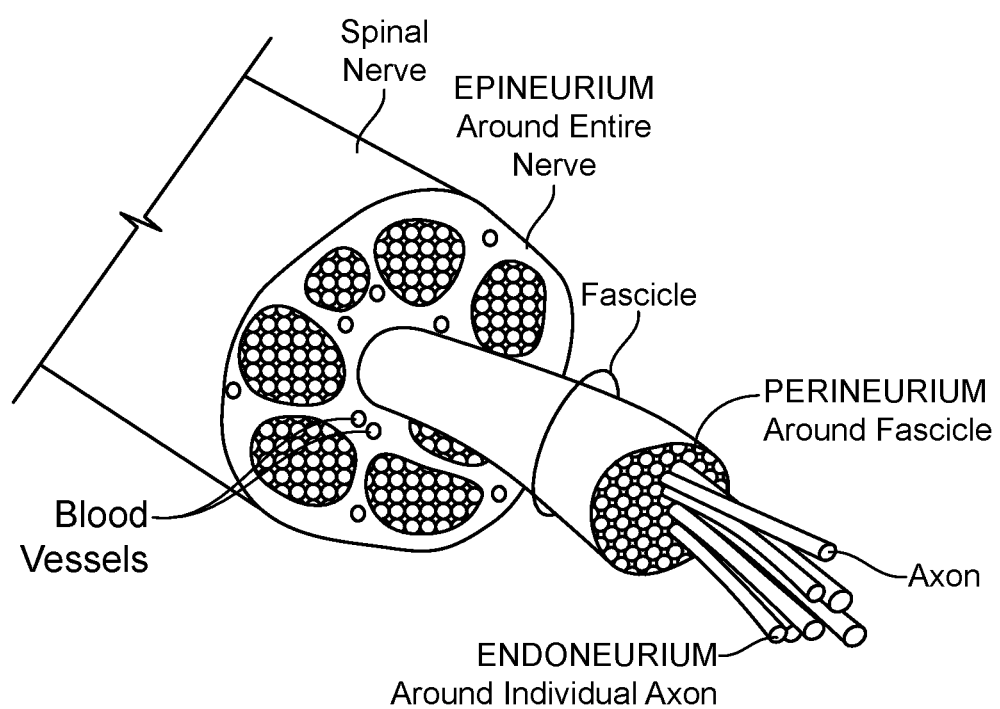
FIG. 2 is a cross-sectional exploded view of a spinal nerve illustrating the epineurium around the entire nerve; fascicle, perineurium around fascicle, axons, endoneurium around an individual axon, and blood vessels.

The morphology may be controlled by using a polymer latex, also called an emulsion, in which polymer particles are dispersed in an aqueous phase, to template the organization of the electrical and ionic conductors, as shown in FIG. 1. Examples of suitable dispersions include elastomeric polymers such as nitrile butadiene rubber, natural rubber, silicone, Kraton-type, silicone acrylic, or polyurethane. Other suitable polymer lattices include polyvinylidene fluoride or polyvinylidene chloride. In such a dispersion, at least 90 mass % of the polymer particles are preferably in the range of 50 nm to 10 μm in diameter. The dispersion is cast and the volatiles (e.g., water) allowed to evaporate. During evaporation, the polymer particles coalesce to form a continuous fill. This process is the common one for creating nitrile gloves.

The electrical and ionic conductors are added to the latex so that they are dispersed in the aqueous phase. Methods known in the art for balancing the pH and selecting any necessary dispersing agents can be used. Suitable electrical conductors are those that have high aspect ratio and are readily dispersed into aqueous solutions and include carbon nanotubes, graphene and graphite structures, and metal nanowires. Suitable ionic conductors include sodium hyaluronate, also called hyaluronic acid, fluorosulfonic acids like Nafion™, sulfated polysaccharides and other mucoadhesive type compounds, or other phosphonic polyvinylsulfonic acids. Likewise, anisotropic ionic conductive particles like graphene oxide and modified graphene oxide may be used. In some embodiments, HA is preferred due to its tendency to hydrate with the skin, improving the skin contact.

By adding electrical and ionic conductors to the dispersed phase of the latex, the conductors tend to coat the surface of the polymer particles, but not penetrate. As the latex is dried, the conductors tend to be confined at the interfaces, creating an interconnecting network, where the major phase is elastomeric and a connected thin, layer phase is the electronic/ionic conductors.

The morphology of this network can be modified by changing the particle size of the polymer in the latex. Larger particle sizes require less conductor to reach an interconnected phase. The film formation temperature is also a tunable parameter that can be used to modify the kinetics to achieve various kinetically trapped states. Other methods to achieve better than random mixing include self-assembling or self-stratifying coatings.

In preferred embodiments, carbon nanotubes are the electrical conductors and hyaluronic acid (HA), or other glycosaminoglycan, along with moisture and ions, is the ionic conductor. Preferably, the MIECs have high conductivity of at least 1000 mS/cm, preferably at least 2000 mS/cm, or in the range of 2000 mS/cm to about 4000 mS/cm is desirable. In some preferred embodiments, the MIECs have high moisture retention such that the composite may absorb at least 20% water, up to 50% by mass water (corresponding to 100% of the weight of the dry composite), in some embodiments 20% to 50%, or 35% to 50% water.

In some embodiments, the MIEC can be further characterized by any one or any combination of the following: the electrode comprising 0.1 to 2 wt % CNTs, preferably 0.2 to 1 wt %, in some embodiments 0.5 to 0.8 wt % CNTs; the electrode comprising 0.1 to 5 wt % glycosaminoglycan, preferably 0.4 to 4 wt %, in some embodiments 0.7 to 3 wt % glycosaminoglycan; the electrode comprising 10 to 60 wt % water, preferably 20 to 50 wt %, in some embodiments 30 to 50 wt % water; the electrode comprising a mass ratio of glycosaminoglycan to CNT in the range of 0.5 to 5, preferably 1 to 3, and in some embodiments 1.5 to 2.5; the electrode comprising at least 0.01 wt % Na, or 0.01 to 2 wt % Na, in some embodiments 0.1 to 1 wt % Na; wherein the electrode has a thickness and two major surfaces; and wherein at least 30 wt % of the CNTs are disposed on a major surface or within the 10% of the thickness near a major surface; wherein the electrode possesses a conductivity of 1000 mS/cm to about 3000 mS/cm that changes by less than 10% after 5 strain cycles of extending the material by 50% and allowing the material to contract; wherein the electrode possesses a ratio of partial conductivity of a charge carrier to the total conductivity, transference number, $t_i$ of at least 0.10, preferably at least 0.13, in some embodiments in the range of 0.10 to about 0.20 or 0.15 to about 0.20.

In some embodiments the electrode comprises one or more of the following: wherein the electrode has a top and bottom surface, the bottom surface is adapted to contact the skin of a patient, and the electrode has a graded structure with an increasing ratio of ionic conductor to electrical conductor from the top to the bottom of the electrode; wherein the gradient is prepared by layer-by-layer fabrication of the electrode, with increasing levels of ionic conductor in successive layers; preferably having at least 3 layers or at least 5 layers; wherein the elastomeric particles comprise nitrile butadiene rubber, natural rubber, silicone, Kraton-type, silicone acrylic, polyvinylidene fluoride, polyvinylidene chloride, or polyurethane, or combinations thereof; wherein, in the emulsion prior to curing, at least 90 mass % of the polymer particles are in the size range of 50 nm to 10 μm in diameter; wherein the electrical conductors have a number average aspect ratio of height to the smallest width dimension of at least 10; wherein the electrical conductor comprises carbon nanotubes, graphene, graphite structures, and metal nanowires, and combinations thereof; wherein the ionic conductor comprises hyaluronic acid, fluorosulfonic acids like Nafion™, sulfated polysaccharides and other mucoadhesive type compounds, or other phosphonic polyvinylsulfonic acids, and combinations thereof; wherein the polymeric or elastomeric polymer comprises an adhesive polymer or wherein the electrode further comprises an adhesive polymer; and wherein the coalesced polymeric particles comprise a fluoropolymer.

The term "carbon nanotube" or "CNT" includes single, double and multiwall carbon nanotubes and, unless further specified, also includes bundles and other morphologies. The invention is not limited to specific types of CNTs. The CNTs can be any combination of these materials, for example, a CNT composition may include a mixture of single and multiwall CNTs, or it may consist essentially of DWNT and/or MWNT, or it may consist essentially of SWNT, etc. CNTs have an aspect ratio (length to diameter) of at least 50, preferably at least 100, and typically more than 1000. In some embodiments, a CNT network layer is continuous over a substrate; in some other embodiments, it is formed of rows of CNT networks separated by rows of polymer (such as CNTs deposited in a grooved polymer substrate). The CNTs may be made by methods known in the art such as arc discharge, CVD, laser ablation, or HiPco.

Glycosaminoglycans are long unbranched polysaccharides consisting of a repeating disaccharide unit. The repeating unit (except for keratan) consists of an amino sugar (N-acetylglucosamine or N-acetylgalactosamine) along with a uronic sugar (glucuronic acid or iduronic acid) or galactose. Glycosaminoglycans are highly polar. Anionic glycosaminoglycans are characterized by having at some hydroxyl protons replaced by a counter ion; typically an alkali or alkaline earth element. Examples of glycosaminoglycans include: β-D-glucuronic acid, 2-O-sulfo-β-D-glucuronic acid, α-L-iduronic acid, 2-O-sulfo-α-L-iduronic acid, β-D-galactose, 6-O-sulfo-β-D-galactose, β-D-N-acetylgalactosamine, β-D-N-acetylgalactosamine-4-O-sulfate, β-D-N-acetylgalactosamine-6-O-sulfate, β-D-N-acetylgalactosamine-4-O, 6-O-sulfate, α-D-N-acetylglucosamine, α-D-N-sulfoglucosamine, and α-D-N-sulfoglucosamine-6-O-sulfate. Hyaluronan is a particularly preferred glycosaminoglycan and representative of its class.

Sodium hyaluronate is the sodium salt of hyaluronic acid (HA). Hyaluron is a viscoelastic, anionic, nonsulfated glycosaminoglycan polymer (shown below). It is found naturally in connective, epithelial, and neural tissues. Its chemical structure and high molecular weight make it a good dispersing agent and film former. CNT/HA aqueous dispersion and phase diagram has been reported in the literature (Moulton et al. J. Am. Chem. Soc. 2007, 129(30), 9452). These dispersions may be used to create conductive films by casting the solution onto a substrate and allowing it to dry. However, the resulting films exhibit blistering, i.e. loss of adhesion, upon exposure to moisture or high humidity. In addition, they suffer from resistance fluctuations that occur as a result of moisture fluctuations, as HA can expand and contract, changing the junction resistance between CNT-CNT contacts.

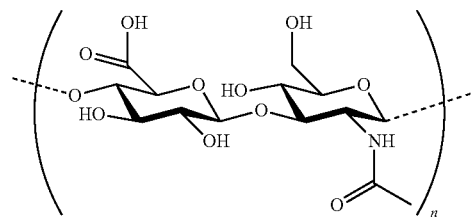

Materials such as sodium hyaluronate are natural products. These may be isolated from animal sources or extracted from bacteria.

The invention is often characterized by the term "comprising" which means "including," and does not exclude additional components. For example, the phrase "a dispersion comprising CNTs and an anionic glycosaminoglycan" does not exclude additional components and the dispersion may contain, for example, multiple types of glycosaminoglycan. In narrower aspects, the term "comprising" may be replaced by the more restrictive terms "consisting essentially of" or "consisting of."

In some embodiments, the ionic element is organized into a gradient structure, getting progressively richer as the material gets closer to the skin. The electrode performance is improved by introducing a smooth transition from electronic conduction interface (from the current collector/Electrode interface) to ionic conduction interface (from the skin-to-electrode-interface). A gradient can be prepared by layer-by-layer fabrication of the electrode, with increasing levels of ionic conductor in successive layers.

Transdermal Drug Delivery, Wound Healing

Iontophoresis is a means by which charged substances are transported across the skin by using a voltage gradient, which allows electrophoresis and/or electro-osmosis. Generally, the devices employ two electrodes that are placed in contact with the skin and connect to a power supply/current control device. One electrode is the drug-delivering electrode and the other is a counter electrode on a different skin site. In an anodal iontophoretic device the drug-delivery electrode is an anode/donor reservoir with a positively charged drug in solution, and the counter electrode is a cathode reservoir. With an electric current, cations move away from the anode and into the skin, and negatively charged ions move from the body into donor reservoir. The reverse is also possible, with anions moving from the dressing into the body. DC current, preferably between approximately 1-4 mA, is needed for delivery. There is a limit to the current density the patient can tolerate. Thus, electrochemical coupling to the skin can be important.

The applied potential causes the charged species, such as drugs, to migrate from bulk (reservoir) to skin-electrode interfacial (wounded area) prompting drug to diffuse at a rate into human body according to gradient value tailored by electrical potential value. In the absence of any electrical field, there is not a strong driving force to promote specie diffusion from reservoir to wounded area (though could still be useful as a wound dressing). Also, in the presence of an electrical field, pores in the skin are opened by a process called electroporation, which promotes skin permeability, which further enhances diffusions.

Generally, in the absence of an electric field, diffusion alone is insufficient to transport the drug or therapeutic agent from the MIEC.

Traditional electrodes are often Ag/AgCl and use a hydrogel to help couple to the skin. The hydrogel increases the electrochemical surface area of the Ag/AgCl electrode, which itself has a low geometric surface area. However, these systems have limitations for long-term stability, coupling with some drugs, and total efficacy. Solid electrolytes are known in the prior art (e.g. U.S. Pat. No. 5,376,107). Solid electrolytes can solve problems of gel and/or liquid based systems; however, transport is more limited and the coupling is not as good.

We have addressed the problem of maintaining a high electrochemical surface area and good contact with the skin by using mixed ionic electronic conductors comprised of a solid electrolyte mixed on a molecular level with electric conductors. By selecting the appropriate electrolyte, the system can also retain moisture which enhances permeability of the skin. The MIEC is prepared by co-dispersing an anisotropic conductive filler, such as carbon nanotubes (CNTs), graphene, or silver nanowires with an ionic conducting polymer such as sodium hyaluronate, in an aqueous dispersion. To this blend can be added one or more drugs or therapeutic agents. Therapeutic agents may include any of those that are commonly delivered by iontophoresis, which include, but are not limited to hydrocortisone, lidocaine, salicylates, dexamethasone, sumatriptan, negatively charged proteins, or any agent that may be beneficial to pass through the skin. The MIEC may further contain optional resins and/or adhesives to improve the film-formation properties. The resin also encapsulates the drug into a solid form. Appropriate resins include typical pressure sensitive adhesive polymers such as acrylics, polyolefins, silicones, or polyurethanes. Preferably, the drug or therapeutic agent comprises an ionic moiety. Examples of drugs or therapeutic agents (note that therapeutic agents is a broad term and includes drugs as well as any compounds that are used to improve health, plant extracts) comprise those identified as suitable for iontophoresis such as identified by US Published Patent Applications Nos. 20180271983 and 20180271777. These have been described in part as: anesthetics, fat removal compounds, nutrients, nonsteroidal anti-inflammatory drugs (NSAIDs) agents for the treatment of migraine, hair growth modulators, antifungal agents, anti-viral agents, vaccine components, tissue volume enhancing compounds, anti-cellulite therapeutics, wound healing compounds, compounds useful to effect smoking cessation, agents for prevention of collagen shrinkage, wrinkle relief compounds such as Botox, skin-lightening compounds, compounds for relief of bruising, cannabinoids including cannabidiols for the treatment of epilepsy, compounds for adipolysis, compounds for the treatment of hyperhidrosis, acne therapeutics, pigments for skin coloration for medical or cosmetic tattooing, sunscreen compounds, hormones, insulin, corn/callous removers, wart removers, and generally any therapeutic or prophylactic agent for which transdermal delivery is desired or combinations thereof. As noted above, the delivery may simply effect transport across the skin or nails or hair follicles into a localized subdermal location, such as treatment of nail fungus or modulation of hair growth, or may effect systemic delivery such as is desirable in some instances where vaccines are used. For administration of anesthetics, typical active ingredients include a local anesthetic agent or combination of local anesthetic agents. The local anesthetic agent may be one or more of the following: benzocaine, lidocaine, tetracaine, bupivacaine, cocaine, etidocaine, mepivacaine, pramoxine, prilocaine, procaine, chloroprocaine, oxyprocaine, proparacaine, ropivacaine, dyclonine, dibucaine, propoxycaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof. Combinations of anesthetic agents may also be used.

The acylation of protein thus provides a negative charge to the protein by virtue of liberating the carboxyl group not bound to the protein. Typical suitable anhydrides include maleic anhydride, succinic anhydride, glutaric anhydride, citraconic anhydride, methylsuccinic anhydride, itaconic anhydride, methylglutaric anhydride, phthalic anhydride and the like. Any dicarboxylic anhydride is suitable; preferred are succinic anhydride and glutaric anhydride. The use of dicarboxylic acyl chlorides is theoretically possible, but these tend to be relatively abrasive, and the use of anhydrides is preferred.

Additional representative active agents include, by way of example and not for purposes of limitation, bepridil, diltiazen, felodipine, Isradipine, nicardipine, nifedipine, nimodipine, nitredipine, verapamil, dobutamine, isoproterenol, carterolol, labetalol, levobunolol nadolol, penbutolol, pindolol, propranolol, solatol, timolol, acebutolol, atenolol, betaxolol, esmolol, metoprolol, albuterol, bitolterol, isoetharine, metaproterenol, pirbuterol, ritodrine, terbutaline, alclometasone, aldosterone, amcinonide, beclomethasone dipropionate, betamethasone, clobetasol, clocortolone, cortisol, cortisone, corticosterone, desonide, desoximetasone, 11-desoxycorticosterone, 11-desoxycortisol, dexamethasone, diflorasone, fludrocortisone, flunisolide, fluocinolone, fluocinonide, fluorometholone, flurandrenolide, halcinonide, hydrocortisone, medrysone, 6a-methylprednisolone, mometasone, paramethasone, prednisolone, prednisone, tetrahydrocortisol, triamcinolone, benoxinate, benzocaine, bupivacaine, chloroprocaine, cocaine, dibucaine, dyclonine, etidocaine, isobutamben, lidocaine, mepivacaine, pramoxine, prilocaine, procaine, proparacaine, tetracaine, zolamine hydrochloride, alfentanil, choroform, clonidine, cyclopropane, desflurane, diethyl ether, droperidol, enflurane, etomidate, fentanyl, halothane, isoflurane, ketamine hydrochloride, mepridine, methohexital, methoxyflurane, morphine, propofol, sevoflurane, sufentanil, thiamylal, thiopental, acetominophen, allopurinol, apazone, aspirin, auranofin, aurothioglucose, colchicine, diclofenac, diflunisal, etodolac, fenoprofen, fllurbiprofen, gold sodium thiomalate, ibuprofen, indomethacin, ketoprofen, meclofenamate, mefenamic acid, meselamine, methyl salicylate, nabumetone, naproxen, oxyphenbutazone, phenacetin, phenylbutazone, piroxican, salicylamide, salicylate, salicylic acid, salsalate, sulfasalazine, sulindac, tolmetin, acetophenazine, chlorpromazine, fluphenazine, mesoridazine, perphenazine, thioridazine, trifluorperazine, triflupromazine, disopyramide, encainide, flecainide, indecanide, mexiletine, moricizine, phenytoin, procainamide, propafenone, quinidine, tocainide, cisapride, domperidone, dronabinol, haloperidol, metoclopramide, nabilone, prochlorperazine, promethazine, thiethylperazine, trimethobenzamide, buprenorphine, butorphanol, codeine, dezocine, diphenoxylate, drocode, hydrocodone, hydromorphone, levallorphan, levorphanol, loperamide, meptazinol, methadone, nalbuphine, nalmefene, nalorphine, naloxone, naltrexone, oxybutynin, oxycodone, oxymorphone, pentazocine, propoxyphene, isosorbide dinditrate, nitroglycerin, theophylline, phenylephrine, ephidrine, pilocarpine, furosemide, tetracycline, chlorpheniramine, ketorolac, ketorolac tromethamine, bromocriptine, guanabenz, prazosin, doxazosin, flufenamic acid, benzonatate, dextromethorphan hydrobromide, noscapine, codeine phosphate, scopolamine, minoxidil, combinations of the above-identified active agents, and pharmaceutically acceptable salts thereof.

Other representative agents include, but are not limited to, benzodiazepines, such as alprazolan, brotizolam, chlordiazepoxide, clobazam, clonazepam, clorazepate, demoxepam, diazepam, flumazenil, flurazepan, halazepan, lorazepan, midazolam, nitrazepan, nordazepan, oxazepan, prazepam, quazepan, temazepan, triazolan, pharmaceutically acceptable salts thereof, and combinations thereof; anticholinergic agents such as anisotropine, atropine, belladonna, clidinium, cyclopentolate, dicyclomine, flavoxate, glycopyrrolate, hexocyclium, homatropine, ipratropium, isopropamide, mepenzolate, methantheline, oxyphencyclimine, pirenzepine, propantheline, telezepine, tridihexethyl, tropicamide, combinations thereof, and pharmaceutically acceptable salts thereof; estrogens, including but not limited to, 17p-estradiol (or estradiol), 17a-estradiol, chlorotrianisene, methyl estradiol, estriol, equilin, estrone, estropipate, fenestrel, mestranol, quinestrol, estrogen esters (including but not limited to estradiol cypionate, estradiol enanthate, estradiol valerate, estradiol-3-benzoate, estradiol undecylate, and estradiol 16,17-hemisuccinate), ethinyl estradiol, ethinyl estradiol-3-isopropylsulphonate, pharmaceutically acceptable salts thereof, and combinations thereof; androgens such as danazol, fluoxymesterone, methandrostenolone, methyltestosterone, nandrolone, nandrolone decanoate, nandrolone phenproprionate, oxandrolone, oxymetholone, stanozolol, testolactone, testosterone, testosterone cypionate, testosterone enanthate, testosterone propionate, 19-nortestosterone, pharmaceutically acceptable salts thereof, and combinations thereof; and progestins such as cingestol, ethynodiol diacetate, gestaclone, gestodene, bydroxyprogesterone caproate, levonorgestrel, medroxyprogesterone acetate, megestrol acetate, norgestimate, 17-deacetyl norgestimate, norethindrone, norethindrone acetate, norethynodrel, norgestrel, desogestrel, progesterone, quingestrone, tigestol, pharmaceutically acceptable salts thereof, and combinations thereof.

The drugs or therapeutic agents can be incorporated into a dressing matrix. One configuration is shown in FIG. 1. In FIG. 1, an MIEC dressing matrix is disposed between an anode and cathode. The MIEC is in contact with a subject's body. The absence of metal ring that is present in a commercially available device makes this device less likely to become damaged during application or storage.

Wound Healing

By incorporating a mixed ionic electronic conductor into wound dressing, the transport reactions related to healing, such as cell, nutrient, oxygen, and water are optimized to occur much faster. Topographical factors and the ionic environment play an important role in dictating transport and repair of wounds.

The MIEC may be formed as a free-standing film. When the ratio of polymer to CNT is in the range of approximately 50 wt. % or less, the dried material will have a network structure, which is often referred to as a CNT network. In preferred embodiments, the MIEC comprises 10-50 wt % CNT, 20-50 wt % ionic conductor, and 5-70 wt % elastomer. The 3D topography of this system and the presence of ionic conductors increases healing transport reaction. Alternatively, a 3D structure can be prepared by electrospinning the CNT/ionic/polymer dispersion, which generates a non-woven mat of nanofibers. With electrospinning, higher loading of polymer can be provided than 50 wt. % because the topography is provided by the process. Finally, the dispersion may also be applied and dried onto to a pre-existing woven or non-woven wound dressing.

The MIEC composition can be applied as a dispersion onto the wound, as the composition hardens, it forms a form-fitting dressing on the wound. A three-dimensional network is prepared by mixing CNTs and ionic conductors and casting into a film or electrospinning; electrospinning will give greater range topographic attributes. Other nutrients and molecules that support cell growth, such as EGF, may be included. Ionic conductors are preferably those that have molecular weight greater than 25,000 g/mol to create a stable system—this is selected to prevent transport of ionic conductors into the wound. Sodium hyaluronate and/or similar molecules are good because they manage the moisture and are biocompatible. This patch is placed in contact with the wound; the system may also be applied to typical dressings such as non-woven or woven gauze.

As an alternative embodiment, bus bars can be applied in a parallel arrangement, allowing the application of current across the dressing, which generates heat by resistive heating. Maintaining a desired temperature, for example in the range of 35 to 40° C. can support wound healing.

(3) Decreasing Interfacial Resistance for Implantable Stimulation or Recording Electrodes. The System May be Placed as a Coating; does not have to be the Whole Material (the Coating May be Only MIEC or Partly MIEC)

We introduce a new method of fabricating a multi-contact deep nerve electrode (DNE). This DNE will adapt biocompatible, mixed ionic electronic conductors based on carbon nanotube (CNTs) composites into the design. These composites will provide electrodes with flexible mechanical properties and low interfacial impedance. This design is targeted to ensure the minimum level of invasiveness to the nerve, but good flexibility to assure chronic mechanic stability of the DNE. This DNE can be surgically inserted into individual fascicle due to its small scale diameter (from 50 to 500 μm for each electrode). The multi-contact design for each electrode will provide the user the capability of monitoring or stimulating different locations along the nerve within each fascicle. This design will not only increase the selectivity of stimulation, but also provide a powerful tool to record the nerve at different levels, allowing researchers to study the functional structure of the nerve. Meanwhile, a multi-electrode cuff holder around the nerve will also be introduced in this disclosure, allowing users to monitor/stimulate multiple fascicles independently.

There are mainly three types of peripheral nerve electrodes to interface the peripheral nerve system: Epineural electrode, Interfascicular electrode, and Intraneural electrode.[1] The best example of an epineural electrode, or cuff electrode, is the Flat Nerve Interfacing Electrode (FINE) from Case Western Reserve University. This type of electrode has multiple contacts around the nerve outside the epinerium, providing the capability of stimulating and recording. Although FINE can provide a limited level of selectivity for stimulating certain fascicles, it still suffers from good selectivity for stimulation in cases where a high number of fascicles are presenting. For example, in human femoral nerve, the number of fascicles are more than 20. FINE electrode provides no access to activate certain fascicles independently.[2] In addition, FINE requires very low-noise electronics to record neural activity around the nerve, since epineurium is highly resistive.[3] As the level of invasiveness increases, the selectivity of the electrodes is improved. A slowly penetrating interfascicular nerve electrode is good an example of a higher invasiveness interfascicular nerve electrode. It cuts the epineurium with multiple blades in order to put electrodes in between the fascicles.[4] The invasiveness gets even higher for intraneural electrodes, like the Michigan shanks and Utah arrays.[4] While getting good selectivity in recording and stimulating, the high level of invasiveness can seriously damage the structure of nerve, making chronic recording not possible. Other peripheral nerve electrodes with high level of invasiveness cannot provide chronic stable recording because of damage to the nerve structure and inflammation responses from the nerve.

In this disclosure, we present a way to fabricate the deep nerve electrode (DNE), which is (1) flexible enough to ensure mechanically chronic stability (2) and has good selectively for both recording and stimulation.

The basic materials technology is a CNT composite. We have demonstrated two highly conductive, mechanically flexible form factors. The first is a thread or filament. High concentration CNT dispersions are lyotropic liquid crystals. When extruded through an orifice into a coagulating bath, they can be drawn into long filaments, with diameters from 10 to 500 um. Due to the high orientation, the filaments have high conductivity, exceeding 25 kS/cm. The second form factor is a coating. Similar dispersions have sufficient viscosity to conformally coat objects, using known methods such as dip-coating, spray-coating, or printing. The dried coating is also quite conductive, approx. 3 kS/cm. Both form factors are mechanically durable and flexible; the can be flexed and bent and maintain their properties.

Figure 3:
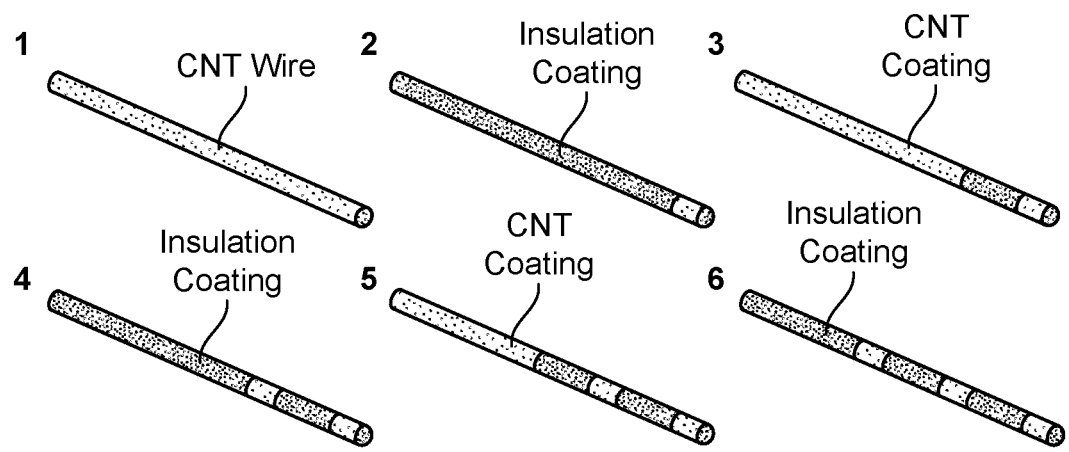
FIG. 3 illustrates a fabrication process of a deep nerve electrode (DNE) with three contacts.

Generally, the limiting factor for an electrode is the efficiency of the electrochemistry at the interface between the electrode and the body. Likewise, the long-term durability of this interface depends on the surface of the electrode. We have recently developed mixed ionic electronic conductors, where the CNTs are embedded in another, biocompatible ionic conductor, such as sodium hyaluronate. These systems lower the interfacial impedance with the electrode. These materials can be used to create a DNE with multiple contacts (FIG. 3). One example is as follows:

1. The core CNT wire is prepared by solution spinning a CNT/ionic conductor dope. The diameter of this filament can be controlled per the design. This core CNT wire provides the architecture for the remaining coating. It will also serve as the first electrode.
2. The CNT wire is coated with a biocompatible, insulating polymer, such as medical-grade silicone polyurethane or thermoplastic polycarbonate polyurethane used for lead insulation in pacemakers. The tip is left uncoated.
3. A CNT/ionic conductor coating is applied, leaving a region of insulated section. The electrical connection for the DNE can also be placed at the bottom during this step.
4. The process of sequentially coating with insulator and conductor is repeated to get the desired number of electrodes.

This CNT based micro electrode can have, for example, a diameter from 10 to 500 µm, depending on the applications. The fabricated electrode can have variable number of contacts, spacing, length and geometry.

Finally, the entire assembly may be coated with a biodegradable lubricant coating to aid with insertion. Alternatively, a final coating with the ionic conductor may be sufficient to assist with insertion.

Figure 4:
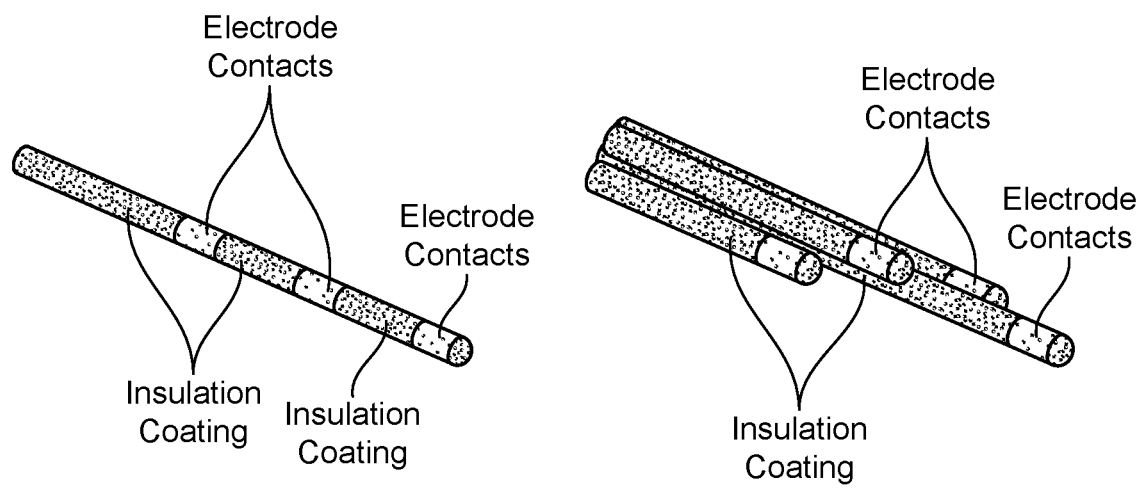
FIG. 4 illustrates two concepts of multi-contact electrode. Left, the one single micro electrode with multiple contacts. Right, several microelectrode forms a larger, multi-contact electrode.

A multi-contact design can allow high level of selectivity for both stimulating and recording. There are two types of multi-contact electrode described here. Following the process 20 mentioned in FIG. 3, a single probe with various contracts can be fabricated, or one could simply stack several single-contact microelectrodes together to form a multi-contact compound electrode (FIG. 4, right side).

Figure 5:
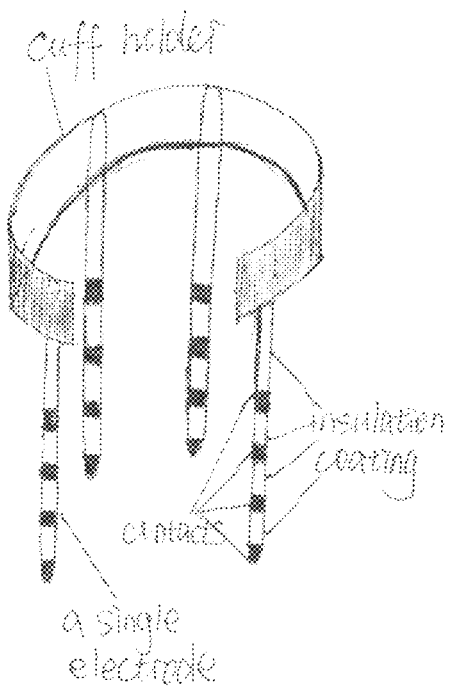
FIG. 5 illustrates a flexible cuff base holding four microelectrodes together.
Figure 6:
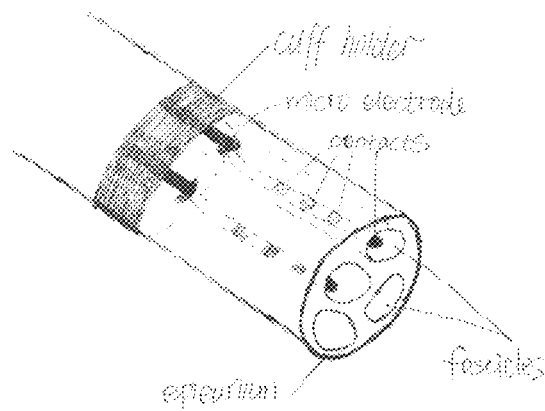
FIG. 6 illustrates a flexible cuff base holds two microelectrodes inserted into the nerve. Each microelectrode shown here has four individual contacts. Each microelectrode is inserted into a different nerve fascicle.

With a single electrode fabricated in this way, one CNT based microelectrode could be used individually or a group of microelectrodes can be used together. A flexible electrode cuff base can be used to hold multiple electrodes around a nerve. In the case of several microelectrodes applied at the same time, a flexible cuff base can hold several electrodes together (FIG. 5). Each electrode acts independently with whatever number of contacts are chosen for each individual electrode. The flexible base with appropriate size is made of biocompatible materials, i.e. biocompatible silicon, with a high level of flexibility so that it can adapt to the size of the target nerve. The flexible cuff holds the microelectrodes around the nerve, and each microelectrode can be inserted into the nerve interfascicularly or intrafascicularly (FIG. 6).

There are five major advantages of the microelectrode and its flexible cuff holder base.

1. This protocol or design allows the fabrication of mechanically flexible microelectrodes with a diameter ranging from 10 to 500 µm. The extremely small size of the electrode diameter will cause the least amount of damage to the nerve structure and potential less immune response of the nerve. This will induce a good chronic recording.
2. The design of multi-contact electrode provides the capability of recording from different levels along the nerve. This enables switching to a different recording site if one of the contacts is broken or not recording any more over time. One electrode enables the recording from inside and outside the nerve fascicles at the same time, if a microelectrode is inserted into the nerve with different contacts located inside and outside the nerve fascicles, or even in different fascicles.
3. The cuff holder around the nerve provides a good mechanical security for each microelectrode. This adds a chronic mechanically stable feature since the microelectrodes will be prevented from pulling out of the nerve due to possible fiction or mechanical force generated by motion between the nerve and nearby muscle or fatty tissue.
4. The cuff holder or base provides the capability of inserting several microelectrodes around the circumference into the nerve to record or stimulate different fascicles. This provides the direct access to certain fascicles and increase the selectivity by nature.
5. Different contacts from different microelectrodes could be selectively activated to conduct the field steering stimulation, so that the fascicles in between the electrodes, the ones without a single microelectrode inserted in, can be electrically stimulated. This approach will further increase the selectivity of this system when used as a stimulating tool.

(4) Non-Invasive Recording Including EEG (3-4 kHz) ECG, EMG (0.5-1 kHz), Bioelectronic Skin Potentials, Etc.

A useful attribute of this technology is its application to various wearable and comfortable forms, such as foam or fabric. No hydrogel is necessary to couple to the skin. Mechanical contact can be provided by applying an elastomeric band around the material or using an elastomer or adhesive as the polymer. This technology addresses motion artifacts in recording electrodes that occurs due to squeeze out of the hydrogel.

(5) Non-Invasive Stimulation

Peripheral nerves can be stimulated to treat neural disease. However, most nerve stimulating interfaces are implanted using an invasive surgery. To overcome this short coming, non-invasive nerve stimulation can be implemented using a hydrogel or other 'wet' conductive interface to transcutaneously stimulate nerves at a reasonable depth below the skin. Unfortunately, this 'wet' electrode—skin interface is suboptimal for long term peripheral nerve stimulation (hours-days). Furthermore, shifts in 'wet' electrodes over time interfere with therapeutic efficacy and the location of applied current fields below the skin. We have developed an interface that is capable of long term current steered non-invasive peripheral nerve stimulation with a mixed ionic dry electrode to treat neural or non-neural disease.

The mixed ionic electronic conductor has advantages over the prior art in that it forms a stable contact. MIECs provide hybrid functionality of ionic & electronic conduction, high electrochemical adhesion, moisture retention, along with mechanical adhesion to improve contact.

Any peripheral nerve that can be reliably activated through the skin and affect physiological function is a candidate for the technology proposed here. For example, peripheral nerve stimulation based therapies to treat disease (e.g. auricular nerve stimulation for atrial fibrillation or trigeminal nerve stimulation for migraine). The nerves that can be specially targeted for non-invasive nerve stimulation are many, and some are listed above for example cases. This technology is proposed to be utilized for nerve stimulation based treatment of disease, and represents a new avenue to electrically activate nerve fibers.

In one example, see FIG. 7, the CNTs and ionic conductor (HA) were mixed with an aqueous nitrile rubber dispersion. A wire is attached to the substrate with adhesive, leaving enough to form a connection exposed. On top of this is then added silver adhesive, labeled "current collector" in the drawing. The silver is allowed to cure. Next the MIEC/elastomer dispersion is applied to that Ag adhesive surface and cured. After curing, this surface becomes the contact with the skin.

Alternatively, the MIEC/elastomer can be directly connected to the wire by placing the wire on a Teflon release layer, casting the MIEC/elastomer and curing. After curing, the resulting material could be readily handled. The electrode was held in contact with the skin by placing a piece of tape over the tops. The following example illustrates a method of making and using an embodiment of the invention:

Dry Electrode Preparation: Carbon Nanotube (CNTs) and Hyaluronic Acid (HA) dispersion prepared by ultrasonic dispersion in water. Mix with nitrile Rubber dispersion (Zeon) by FlacTek® at ~1700 RPM for 30 seconds.

Casting the MIEC A Pt wire was placed on a Teflon mold. The wire was then taped down on the frame of the Teflon mold and the wires were pressed onto the mold, so they would lay flat on the mold. 90 µl of CNTs-HA-Elastomer solution was dispensed straight on the wire The solution was left to cure over the weekend (~24 hours at room temperature).

Two of these electrodes were attached to the skin of a mouse. A modulated pulse was applied of approximately 1-1.5 mA and less than 50 Hz. Showed selective non-invasive modulation of blood pressure without side effects on heart rate using MIEC electrodes.

A more adhesive formulation can be prepared by using a different polymer emulsion. For example, CariFlex™ SIS Emulsion can be used to form the adhesive.

Any of these systems can be applied to electrodes that would usually use a hydrogel. For example, Ag/AgCl can be coated with the MIEC.

6 the Matrix Provides a Useful Means of Storing and Delivery Vaccines to Eliminate Cold Chain.

This concept, in preferred embodiments, addresses issues with cold chain for vaccines by embedding the vaccine in the MIEC. In the first step the vaccine is encapsulated in an ionic polymer. In the second step the encapsulated polymer is mixed with an electronic conductor to form the MIEC. In the third step the MIEC is added to an elastomer and formed into a microneedle skin patch. In the fourth step the microneedle skin patch is formed into desired delivery device. The concept is schematically illustrated in FIG. 8.

The vaccine described in step one includes but not limited to live-attenuated vaccines, inactivated vaccines, subunit, recombinant, polysaccharide, and conjugate vaccines and toxoid vaccines. The ionic polymer described in step include cationic, anionic or the mixture thereof. They are exemplified by but not limited to chitosan, poly (N,N'-dimethyl aminoethyl methacrylate), hyaluronic acid, poly(acrylic acid) and the combination thereof. The encapsulation method described in the first step can be layer by layer coating, particle forming methods such as emulsion, suspension or dispersion. The electronic conductor described in the second step includes but not limited to single walled CNT, multiwalled CNT, fullerenes, graphene, carbon particles, nanoparticles of Cu, Au, Ag and Pt, conducting polymers such as polyaniline, polythiophene, poly pyrrole and their mixture thereof. The elastomers described in the third step includes but not limited to silicone rubber, natural rubber, synthetic rubber, polyurethane elastomer and their mixture thereof.

In preferred embodiments, this method of storing vaccines maintains vaccine activity with no refrigeration.

(7) Epicardial Mesh

Figure 9:
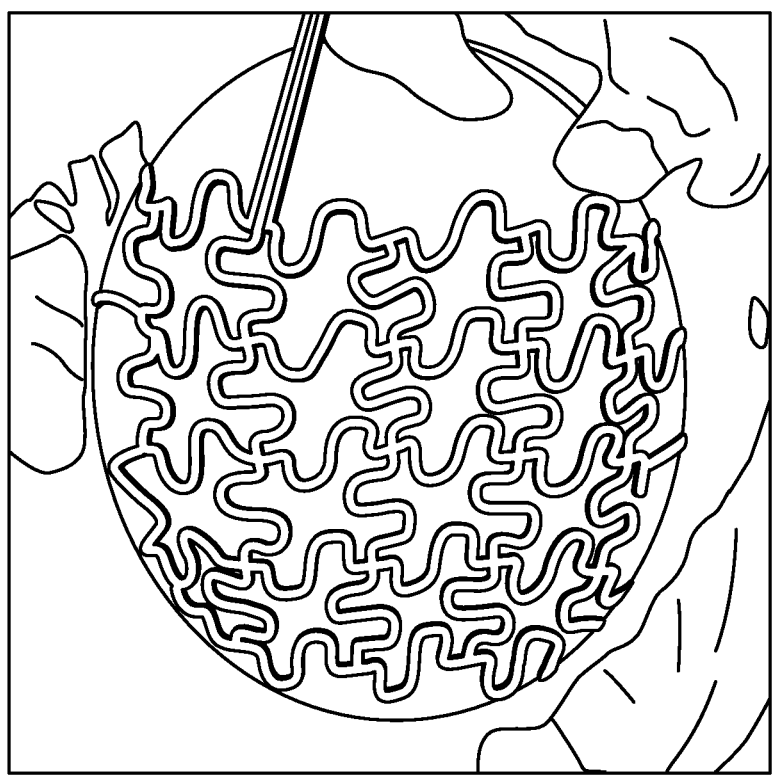
FIG. 9 shows an epicardial mesh (the picture is prior art).

The prior art has described epicardial meshes as a way to deliver electrical impulses to the whole ventricular myocardium, rather than merely to small point electrodes in the ventricles. See FIG. 9. This is carried out by creating conductive and elastomeric materials. Systems have included CNT-based composites, which had insufficient electrical conductivity and/or poor elasticity due to inadequate dispersion. Others have looked at silver nanowire (AgNW) networks dispersed in polymers such as styrene-butadiene-styrene (SBS) rubber, a biocompatible thermoplastic polymer. The AgNW/polymer networks have better electrical conductivity; however, these systems do not provide for an electrochemical response, e.g. the conversion from electronic conduction to ionic conduction; The current in the heart is carried by ions such as Na and K. Thus high bulk DC-conductivity is only one property.

We have applied the use of mixed ionic electronic conductors to control both interfacial resistance and capacitive coupling between the material and the heart. The electronic conductors may be any anisotropic conductor, such as CNT or Ag nanowires. Ag nanowires are preferred when conductivity greater than 2,000 S/cm is desired. Due the method by which these composites are prepared, we can achieve higher conductivity and better retention of mechanical properties than bulk mixing. The electrical and ionic conductors are mixed with polymer emulsions, which can then be cast and/or dried and further processed by melt processing.

(8) Implantable Sensors.

The invention provides a system as an implant or otherwise senses pressure changes. Implantable pressure sensors which are MEMS devices or stiff electronic/semiconductor materials limits the quality of the contact that can be made with soft tissue in the body, and thus limits their sensitivity to pressure changes that are associated with medically important changes, such as tumor growth or biomechanical processes. In contrast, MIECs and MIEC polymer matrix composite systems are designed from soft, biocompatible materials of any geometry. MIECs can be triggered to form continuous networks, such as a hydrogel, in situ, after injection of pre-cured components, such that the composite conforms to the shape of a cavity, recess, or channel in vivo. In other words, the prepolymer MIEC is injected and fills the shape, and then crosslinks once in vivo. The ionic/polyionic component can be selected to possess favorable biocompatibility to allow unperturbed cell growth, or to stimulate growth of cells into the MIEC composite.

Changes in material impedance report for pressure changes within the in vivo microenvironment of the implanted sensor. The MIEC is in close contact with body tissue, when the tissue moves, it puts pressure on the elastic MIEC, causing impedance changes. This change in resistance occurs mainly due to changes in the CNT-CNT junctions (resistive response) but also due to changes in the electrochemical double layer. If the MIEC is configured to record changes in impedance, such as by attaching between parallel bus bars or placing a bias to make a field effect transistor, local pressure changes can be monitored. These MIEC sensor system applications include, but are not limited to: sensing cell growth and particularly for real-time tumor growth monitoring, single cell biomechanics of filipodia or cytoskeletal actin filament formation, blood pressure monitoring with bioinert components, or for monitoring intracranial pressure after injury or surgical intervention.

The sensor is formed from mixed polyionic electronic materials doped into a bioinert polymer matrix that is pre-cured in a desired shape. Dimensions may, in preferred embodiments, be less than 10 μm to avoid foreign body response. In one embodiment, the MIEC body of the sensor is in the shape of a cylinder, preferably having a dimension of 2 μm or less. In another embodiment, the polyionic material is first chemically functionalized with polymerizable side groups, such vinyl, methacrylic, or norbornyl groups that can later be polymerized in situ to fabricate a conformal tissue sensor. The MIEC body of the sensor can have electrical contacts on opposite sides of the MIEC implant; in another variation, the MIEC body of the sensor can be inductively coupled from outside the body.

(11) Sensors—any Kind of Sensor that Will be Electrical Sensing in an Aqueous Environment (Water, Blood, Tissue, Salt Water). Different Sensing Device—Such as but not Limited to Reference or Sensing Electrode for Hydrogen, or Sodium (or Potassium) Electrode Typical ion-sensing requires a two-chamber device where a membrane separates two electrodes at different chemical potential; this results in measurable voltage. Our invention creates a similar kind of phenomenon but on a sub-microscopic level. An ionic conducting material, like Nafion, is dispersed with the electrically conductive material. This eliminates the need for two compartments and greatly simplifies the design. A single compartment cell measures changes in ionic concentration.

The MIEC is on a substrate. The reference electrode is created by attaching wire to the underside of the MIEC, at the interface between the substrate and the MIEC, where it is encapsulated from the environment. The working electrode is created by connecting to the top surface that is exposed to the environment. What is surprising is that there is a difference in the chemical potential between these two surfaces. We hypothesize that this is due to the, largely, two-dimensional structure of CNT networks in MIEC, where conductivity is higher in-plane than through-plane. The ionic conductor serves as the ion-sensing membrane. The MIEC need not be on a substrate, but the reference electrode should be in an encapsulated position.

Figure 10:
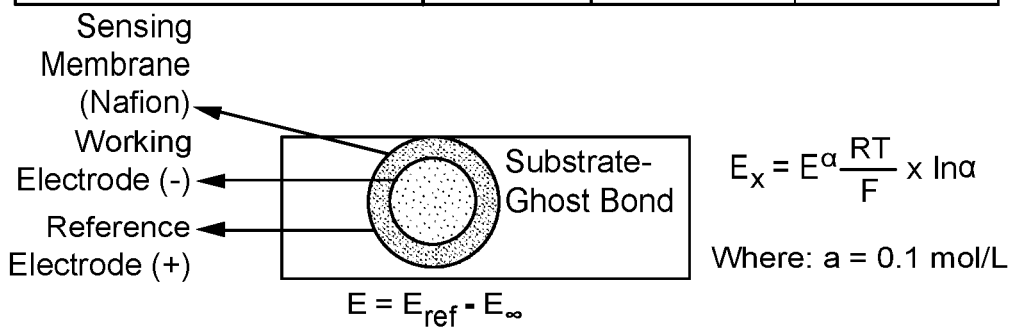
FIG. 10 shows the results of an electrode potential determination for a variety of membranes.
Figure 11:
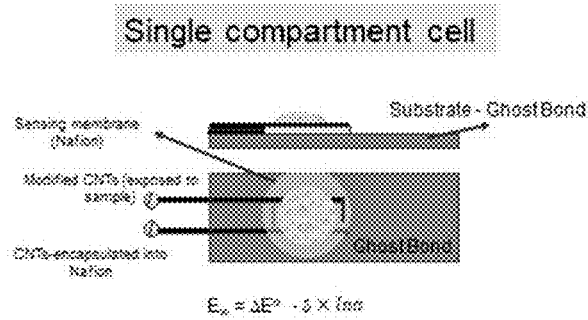
FIG. 11 shows the cross-section of a single compartment cell using an MIEC membrane.
Figure 11:

FIG. 10 shows the results of an electrode potential determination for a variety of membranes. The membrane is placed on a substrate via an adhesive (GhostBond™ in the examples). The sensor, a single compartment cell, illustrated in cross-section in FIG. 11, is capable of being attached to the skin.

Translation and commercialization of chemiresistive sensors based on carbon nanomaterials or SPR sensors have been hampered by poor sensitivity, specificity, and passivation by biofouling. High ionic strength environments create pinned ions at sensor working surface (Helmholtz double layer), which reduces target sensitivity. Moreover, adsorption/binding of off-target species can cause poor specificity and eventual passivation, which further reduces sensitivity. In this invention, active biosensor surfaces (electronic or SPR) are modified with polyionic coatings to reduce false positives and false negatives in complex biological media. Sensing in biological media poses several challenges. Polyionic coatings can improve ion transport and reduce off-target fouling. Techniques include layer by layer assembly and "grafting-from" by radical polymerization. Polyionic coatings include: incorporation or surface grafting of biopolymer polyelectrolyte such as extracellular matrix or polysaccharide materials, Layer-by-layer assembled in methanol of Nafion/branched polyethyleneimine, "Grafting from" SI-ATRP, of sulfo-betaine methacrylate (SBMA) from surface bound bromoisobutyryl bromide. SI-photopolymerization of nanofilms of SBMA/PEGDA after surface tethering photoinitiators. SI-ROMP of carboxynorbornene after surface functionalizing with ROMP initiators.

Figure 12:
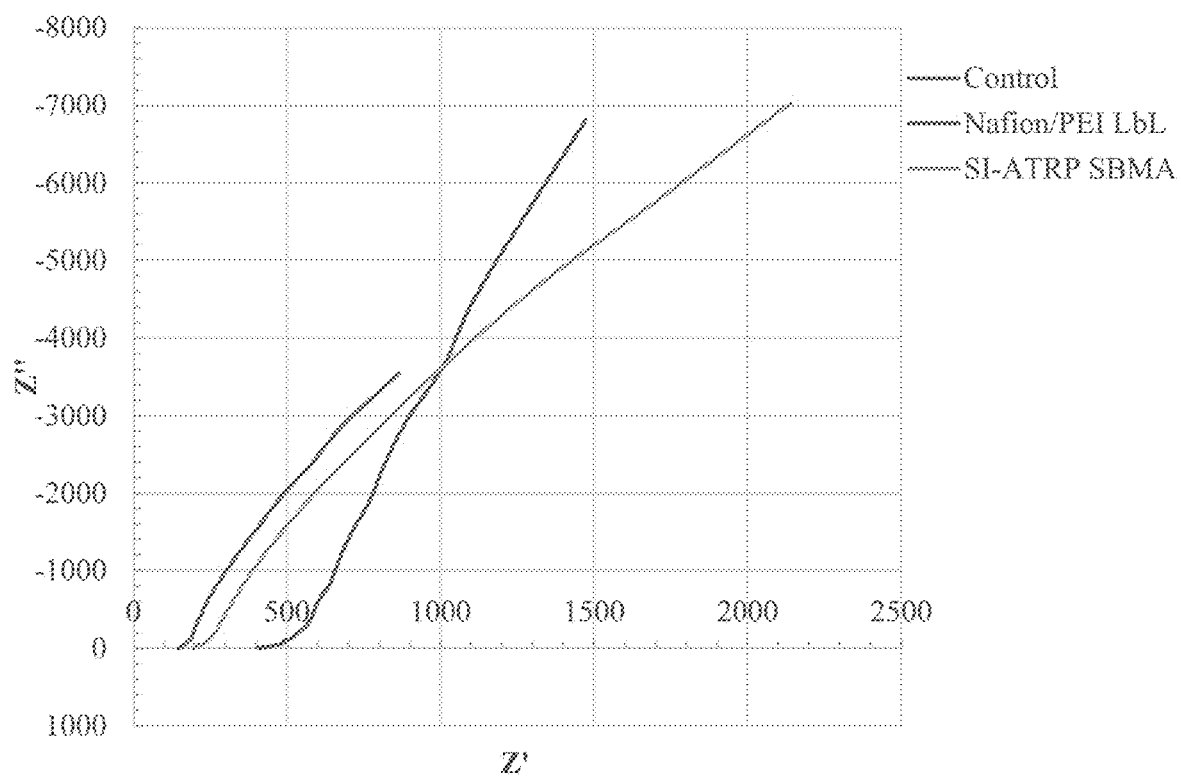
FIG. 12 shows the results of electroimpedance spectroscopy of Z" vs Z' for MIEC control (left), with Nafion/PEI (furthest right on x-axis at 0 on y (Z") axis), and SBMA (center) surface modifications. The cell was set up with a MIEC film on a slide partially submerged in a 0.1M NaCl solution with a submerged Ag/AgCl reference electrode and platinum mesh counter electrode. Units are in ohms.
Figure 13:
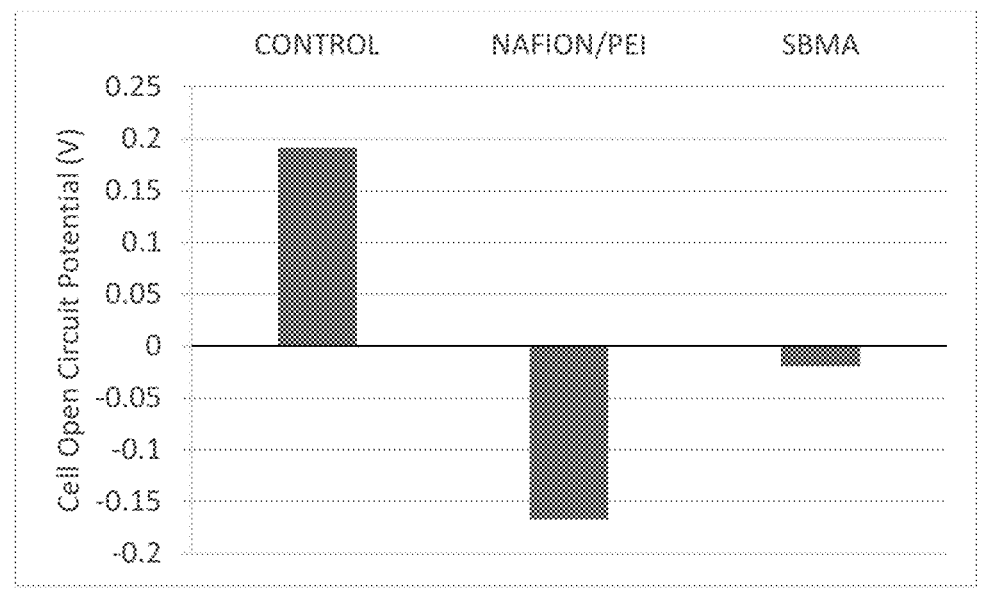
FIG. 13 shows the open circuit potential in an electrolyte cell (0.1M NaCl) of MIEC control and surface modified MIEC films showing the change from control.

For electrochemical sensors, the signal can be further enhanced by creating a mixed ionic electronic conductor, where the aforementioned polyionic coatings are mixed with electrical conductive elements. Mixing polyionic materials with electrical conductive elements can increase the electrical surface area to improve sensitivity. Gradients of increasing proportion of mixed polyionic materials near the outer conductor surface can also show improvements in charge transfer from ionic media into or out of the conductor material. The gradient of electronic/mixed polyionic materials can be further improved by transitioning into the aforementioned coatings or polymeric brushes to extend the gradient of the ionic component into the electrolytic aqueous media. Changes in charge transfer and the cell voltage can be seen in FIGS. 12 and 13 for polyionic surface modifications of Nafion-Polyethyleneimine and Sulfobetaine methacrylate (SBMA) surface coatings grafted on to MIEC composites. The control is the composite without further surface modifications.

For implantable sensors, the MIEC can be mixed with a soft, or low modulus, polymeric matrix to ensure biocompatibility. Typical currently available electrode for implantable sensors are composed of high modulus electronic materials, and have significant translational challenges due to host rejection and fibrous capsule formation around implant. Low modulus elastomers that match or nearly match the modulus of tissue can reduce rejection and graft-vs-host response The low modulus, elastomeric polymeric matrix can include but is not limited to polydimethylsiloxane, polyisoprene, copolymers of styrene-isoprene, or other biocompatible and bioinert matrices. This composite can be fabricated by mixing the electronic and polyionic components with the polymeric matrix that has been emulsified, or by direct dispersion in a common solvent, then casting the mixture to be cured or coagulated by heat, photoinitiation, or by solvent evaporation.

Ionic segments of the polymeric ionic conductor can be grafted on a polymer backbone. The ionic segments can be anionic, cationic or amphoteric. One method of grafting ionic segment is via co-polymerizing ion-containing monomers with non-ion-containing monomers. Another way of grafting ionic segment is via post functionalizing the elastomeric polymer.

Examples of anionic segments include, but not limited to, sulfonic, carboxylic, phosphonic and combinations thereof. Examples of cationic segments includes alkyl ammonium derivatives such as the N,N-dimethyl amino ethyl functionality. Examples of amphoteric segments includes the combination of anionic and cationic segments.

Examples of grafting anionic segments include, but are not limited to, co-polymerizing anion containing monomer such as styrene sulfonic acid with non-ion containing monomers such as styrene and butadiene to produce anion containing styrene-butadiene elastomer, namely sulfonated styrene-butadiene elastomer.

Examples of grafting cationic segments include, but are not limited to, co-polymerizing cation containing monomer such as N,N-dimethyl aminoethyl methacrylate with non-ion containing monomers such as styrene and butadiene to produce cation containing styrene-butadiene elastomer, namely aminated styrene-butadiene elastomer.

Examples of grafting amphoteric segments include, but are not limited to, co-polymerizing anion and cation containing monomer such as styrene sulfonic acid and N,N-dimethyl aminoethyl methacrylate with non-ion containing monomers such as styrene and butadiene to produce amphoteric ion containing styrene-butadiene elastomer, namely sulfonated and aminated styrene-butadiene elastomer.

Examples of post functionalizing the elastomeric polymer include, but are not limited to, treating styrene butadiene elastomer with fuming sulfuric acid to produce anion-containing styrene-butadiene elastomer, namely sulfonated styrene-butadiene elastomer.

(12) Membrane Application for Separation of Different Species Such as Na+; K+, Etc.

Sodium or/and Potassium membrane separation has a principal advantage over other separations that it can occur without external energy input. At equilibrium the chemical potentials of permeating Na+ at the feed and permeate side become the same. For low Na+ concentration, separation means that the partial pressures or permeable species become the same at the feed and permeate side of the membrane.

For an ideal membrane that is ideally permeable for only one species (Na+) the only external energy input needed is the compression work to drive the Na+ to the sequestering location. Mixed-ionic-electronic-conduction membranes are very selective for sodium, high flux, and possible reduced investment costs, thickness preferably <100 μm, more preferably <10 μm. The presence of hyaluronic acid in salt form promotes sodium ion mobility resulting on its diffusion toward low chemical potential side. Due to high affinity of HA to CNTs, the CNTs prevent HA from leaching out from the membrane structure.

What is claimed:

1. A method of treating a human or nonhuman animal, comprising:
   providing an apparatus comprising a MIEC disposed between an anode and cathode;
   wherein the MIEC comprises an electrical conductor, ionic conductor, and elastomeric particles;
   applying the MIEC directly in contact with skin of the human or nonhuman animal; and
   passing an electrical current through the MIEC wherein at least 90 mass % of the elastomeric particles have diameters in a range of 50 nm to 10 μm.

2. The method of claim 1, wherein the current heats the MIEC to a temperature in the range of 35 to 40° C.

3. The method of claim 1, wherein the MIEC comprises a dispersed drug or therapeutic agent; and wherein the current passed through the MIEC increases the permeability of the skin.

4. The method of claim 1, wherein the method does not utilize a hydrogel.

5. The method of claim 1, wherein the MIEC is placed in direct contact with a wound in the skin.

6. The method of claim 1, wherein the electrical conductor has an aspect ratio of at least 10× length compared to height and width.

7. The method of claim 1, wherein the elastomeric particles comprise: nitrile butadiene rubber, natural rubber, silicone, Kraton-type, silicone acrylic, or polyurethane.

8. The method of claim 1, wherein the electrical conductor is selected from the group consisting of carbon nanotubes, graphene and graphite structures, and metal nanowires.

9. The method of claim 1, wherein the ionic conductor comprises sodium hyaluronate.

10. The method of claim 1, wherein the ionic conductor comprises a mucoadhesive compound.

11. The method of claim 1, wherein the MIEC has a conductivity in a range of 2000 mS/cm to 4000 mS/cm.

12. The method of claim 3, wherein the dispersed drug or therapeutic agent comprises: hydrocortisone, lidocaine, salicylates, dexamethasone, sumatriptan, or a negatively charged protein.

13. The method of claim 3, wherein the dispersed drug or therapeutic agent comprises: an anesthetic, fat removal compound, nutrient, nonsteroidal anti-inflammatory drug (NSAID), agent for the treatment of migraine, hair growth modulator, antifungal agent, anti-viral agent, vaccine component, tissue volume enhancing compound, anti-cellulite therapeutic, wound healing compound, compound useful to effect smoking cessation, agent for prevention of collagen shrinkage, wrinkle relief compound, compound for relief of bruising, cannabinoid, compound for adipolysis, compound for the treatment of hyperhidrosis, acne therapeutic, pigment for skin coloration for medical or cosmetic tattooing, sunscreen compound, hormone, insulin, corn/callous remover, wart remover, or combination thereof.

14. The method of claim 3, wherein the dispersed drug or therapeutic agent is selected from the group consisting of: benzocaine, lidocaine, tetracaine, bupivacaine, cocaine, etidocaine, mepivacaine, pramoxine, prilocaine, procaine, chloroprocaine, oxyprocaine, proparacaine, ropivacaine, dyclonine, dibucaine, propoxycaine, chloroxylenol, cinchocaine, dexivacaine, diamocaine, hexylcaine, levobupivacaine, propoxycaine, pyrrocaine, risocaine, rodocaine, pharmaceutically acceptable derivatives thereof, bioisosteres thereof, and combinations thereof.

15. The method of claim 7, wherein the MIEC comprises 10-50 wt % CNT, 20-50 wt % ionic conductor, and 5-70 wt % elastomer.

16. The method of claim 5, wherein the MIEC composition is applied as a dispersion onto a wound where it hardens to form a form-fitting dressing on the wound.

17. The method of claim 5, wherein the MIEC is formed by a method comprising electrospinning a mixture of CNTs and ionic conductors.

18. The method of claim 1, wherein the ionic conductor has a molecular weight greater than 25,000 g/mol.

\* \* \* \* \*